United States Patent [19]

Kuznia

[11] 4,259,721
[45] Mar. 31, 1981

[54] COMPUTER SYSTEM FOR THE IMAGE SYNTHESIS OF A TRANSVERSE BODY SECTION AND METHOD FOR THE OPERATION OF THE COMPUTER SYSTEM

[75] Inventor: Christian Kuznia, Munich, Fed. Rep. of Germany

[73] Assignee: Siemens Aktiengesellschaft, Munich, Fed. Rep. of Germany

[21] Appl. No.: 895,395

[22] Filed: Apr. 11, 1978

Related U.S. Application Data

[63] Continuation-in-part of Ser. No. 876,333, Feb. 9, 1978, abandoned.

[30] Foreign Application Priority Data

Feb. 10, 1977 [DE] Fed. Rep. of Germany ....... 2705640

[51] Int. Cl.² ......................................... G01N 23/00
[52] U.S. Cl. ............................. 364/414; 250/445 T; 358/111; 364/515
[58] Field of Search ..................... 364/414, 527, 515; 250/445 T, 363 S, 369; 358/111

[56] References Cited

U.S. PATENT DOCUMENTS

| | | | |
|---|---|---|---|
| 3,878,373 | 4/1975 | Blum | 364/414 |
| 4,087,694 | 5/1978 | Hellstrom et al. | 250/445 T |
| 4,105,922 | 8/1978 | Lambert et al. | 250/445 T |
| 4,129,783 | 12/1978 | Houston | 250/445 T |

*Primary Examiner*—Errol A. Krass
*Attorney, Agent, or Firm*—Kenyon & Kenyon

[57] ABSTRACT

Coordinated with the detectors of a computer system for tomography is a multimicroprocessor which contains a computer module with a microprocessor as well as coupling, program, and data memories for each individual detector. Coordinated with the identical computer modules is one common control computer which carries out the individual phases of the image reconstruction in a three-phase operation (SMS system) permitting a transverse body section in which the information from each of the scans is processed simultaneously to be constructed in only a few seconds.

9 Claims, 2 Drawing Figures

COMPUTER SYSTEM FOR THE IMAGE SYNTHESIS OF A TRANSVERSE BODY SECTION AND METHOD FOR THE OPERATION OF THE COMPUTER SYSTEM

RELATED APPLICATIONS

This application is a continuation in part of application Ser. No. 876,333 filed Feb. 9, 1978 and now abandoned.

BACKGROUND OF THE INVENTION

This invention relates to a computer system for the image synthesis of a transverse body section with image elements which are successively penetrated by the rays in the image plane in various directions, and detected by an arrangement of several detectors in general and more particularly to an improved computer system of this nature.

A computer system for image synthesis is disclosed in U.S. Pat. No. 3,983,398. Producing tomographic X-ray pictures by digital computing methods requires extensive computation. The computations include filtering the sequence of input signals from the individual exposures, computation of the correlated image element addresses, and adding both the image information and image corrections. More than five minutes are needed by a conventional small computer to produce a tomograph picture of, say, 160×160 image elements.

SUMMARY OF THE INVENTION

Now, it is an object of the present invention to reduce to a few seconds the time required to compute a tomometry image.

The hitherto applied solutions of this problem were the use of faster computer processors. While such units can reduce the computation time considerably, the equipment is relatively expensive. Moreover, the capabilities of semiconductor technology impose limits on the computing speed of a single processor.

Therefore, according to the present invention, the above problem is solved by coordinating with the detectors a multimicroprocessor arrangement which contains one microprocessor for each individual detector, forming a computer module with a coupling, program, and data memory as well as a bus switch. One common control computer, with which a program memory and an image synthesis memory are coordinated, is provided for the identical computer modules. Each computer module is connected via the bus switch to a common system bus which assumes the function of an address, data, and control bus and is managed by the control computer. The processed information is stored in the coupling memory prior to the exchange.

The electrical signal furnished by a detector such as for X-rays, electron or light rays is converted into a digital signal and fed to its associated computer module via a suitable I/O interface. The information from a scan is corrected in the computer modules simultaneously and independently of each other. This correction is necessary because of the nonlinearity of the detectors and for radiation hardening. It equalizes the uneven absorption of rays of different wave lengths by the various parts of the body. The correction is also required because of the anisotropy in the radiation characteristic of the radiation source used, and for the compensation of different geometry factors of the overall arrangement.

The corrected information from the individual computer modules is subsequently folded in a three-phase operation controlled by the common control computer. Only the control computer operates during the first control phase. It establishes the initial state of the computer modules and signals the problem they will have to solve in the succeeding autonomous phase. In this second phase the microprocessors of the modules simultaneously and independently of each other solve problems assigned to them by their program and then signal the control computer that they have completed their program with a stop signal. As soon as the control computer has received a stop signal from one or from a selection of microprocessors determined by the circuit, the data exchange between the memories of the computer modules and, if applicable, the image synthesis memories takes place in the third phase, the information transmission phase, controlled by the control computer.

Then a part image of the entire body section is constructed with the folded information in each module. During both folding and image construction all computer modules work in parallel and simultaneously. The next scan can already be put in at a shorter time interval, which may be as short as 3 msec.

Instead of folding the corrected information, the information from the fan-shaped beam may also be rearranged so as to appear as parallel beam scan values and may then be folded without specific correction factors and be further processed later in the image synthesis.

After folding the scans the modified detector data are stored in the memories of the computer modules. Since every piece of information obtained is correlated with several image areas, the individual data must be added up in defined places of the final picture. The manner of correlating the data with the image area is determined by the program given to the microprocessor of the computer module. In one special embodiment of the computer system a part area of the entire body section may be assigned to each module. Therefore, if 128 detectors and, hence, modules are present, for instance, each module memory contains 128th part of the entire body section.

To compute the image element addresses, the correlation of the folded data with the associated image elements may be stored in this computer system in a read only memory (ROM). The modified data are then added up in the module memories to the correct places in the part image matrix.

In the last section of the image processing program the part images from the individual modules are stored in the image synthesis memory via the common system bus. Upon the conclusion of this operation the finished tomograph picture is stored in the image synthesis memory. From this memory the picture can be fed to a visual display or also to a printer. Due to the fact that the data from the individual detectors can be processed immediately after each exposure, it takes the computer system only a few seconds to produce the picture.

DETAILED DESCRIPTION OF THE INVENTION

Figure 1:
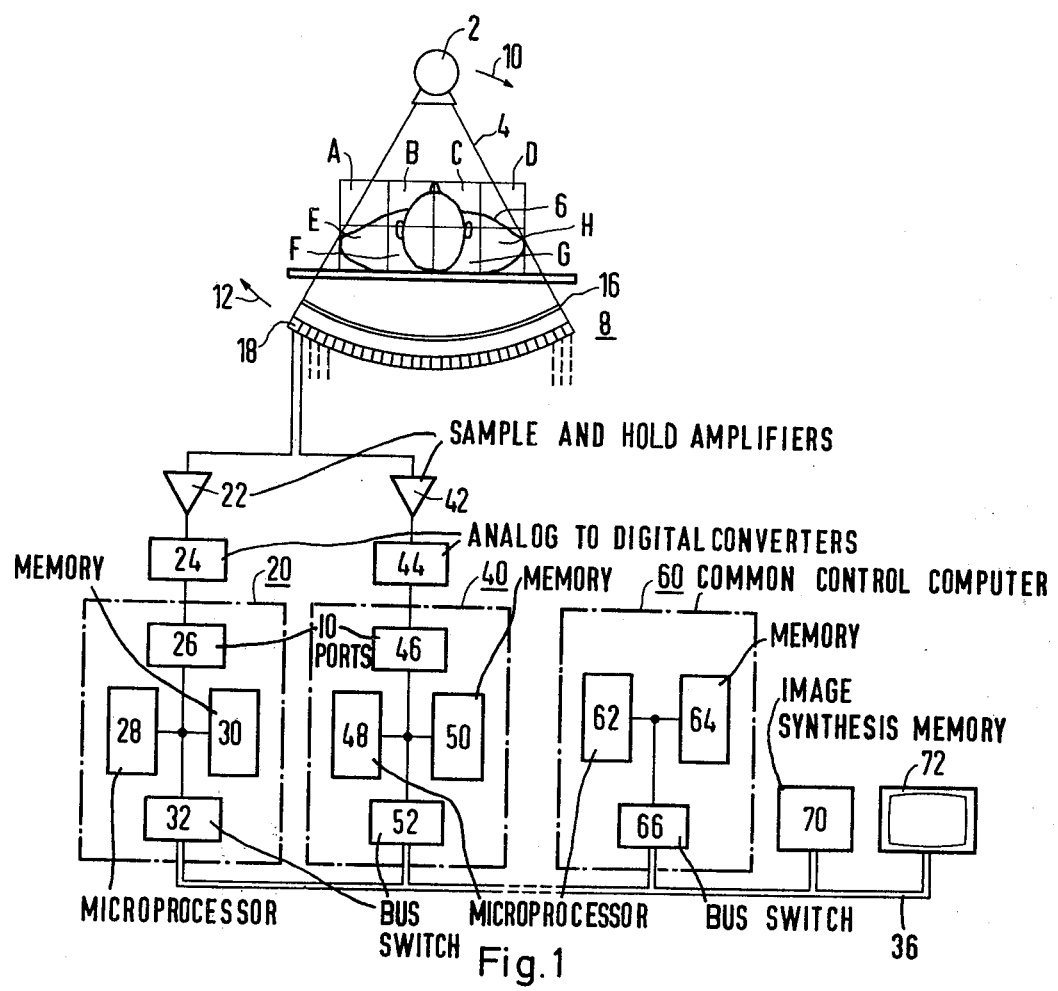
FIG. 1 is a block diagram of an arrangement for producing a transverse body section according to the present invention.

In FIG. 1, a radiation source 2 such as for X-rays or gamma rays, a fan-shaped beam 4, a living body such as of a person whose transverse section is to be taken 6, and a detector system 8 are shown. The radiation source 2 with the detector system 8 is mounted so as to be rotatable about an axis perpendicular to the drawing plane, as indicated in the Figure by arrows 10 and 12. To produce the transverse body section the system is rotated about the body 6 either continuously or stepwise in predetermined angular increments of, say, 1°, an exposure being made for each increment.

The detector system 8 contains a linear arrangement of, say, 256 detectors 18, each furnishing an electrical signal analogous to the impinging radiation. Detectors 18 for X-rays of gamma rays may be used. The radiation 4 from the radiation source 2 is preferably transformed into light or also electron rays, however. A scintillator 16, for example, may be provided for this purpose, in which photons fed to the detectors 18 are released by the radiation 4.

In another embodiment the photons may release electrons in a photocathode not shown in the Figure which are accelerated in a vacuum tube and then fed to the detectors 18.

One computer module is assigned to each detector 18. For the sake of simplicity only 2 of the 256 computer modules are shown in the Figure and marked 20 and 40, respectively. They will preferably be identical in design. Generally, the output signal furnished by one of the detectors 18 is fed via amplifiers 22 and 42, respectively, which may preferably be of the sample and hold type, to an analog-to-digital converters 24 and 44, respectively, which convert the analog electrical input signal into a corresponding sequence of digital signals. This digital signal is fed to the microprocessors 28 and 48 of the computer modules 20 and 40 via I/O ports 26 and 46, respectively. Coordinated with the microprocessors 28 and 48, serving as the single computer of the modules 20 and 40 are memories 30 and 50, respectively, each of which should contain both a coupling memory and a program and data memory. The memories are designed as traffic and work memories, containing both random access memories and read only memories. The microprocessors 28 and 48 of the computer modules are connected to a system bus 36 via bus switches 32 and 52, respectively, which connects all computer modules to a common control computer 60.

The control computer 60 also contains a microprocessor 62 as a single computer and a program memory 64. It is connected to the system bus 36 via a bus switch 66. The processed information is stored in an image synthesis memory 70 designed as mass memory which may also be contained in the control computer 60.

The information stored in the image synthesis memory 70 is supplied via a recall not shown in the Figure to an image reproduction device 72 which may be a visual display or also a printer, for example.

Figure 2:
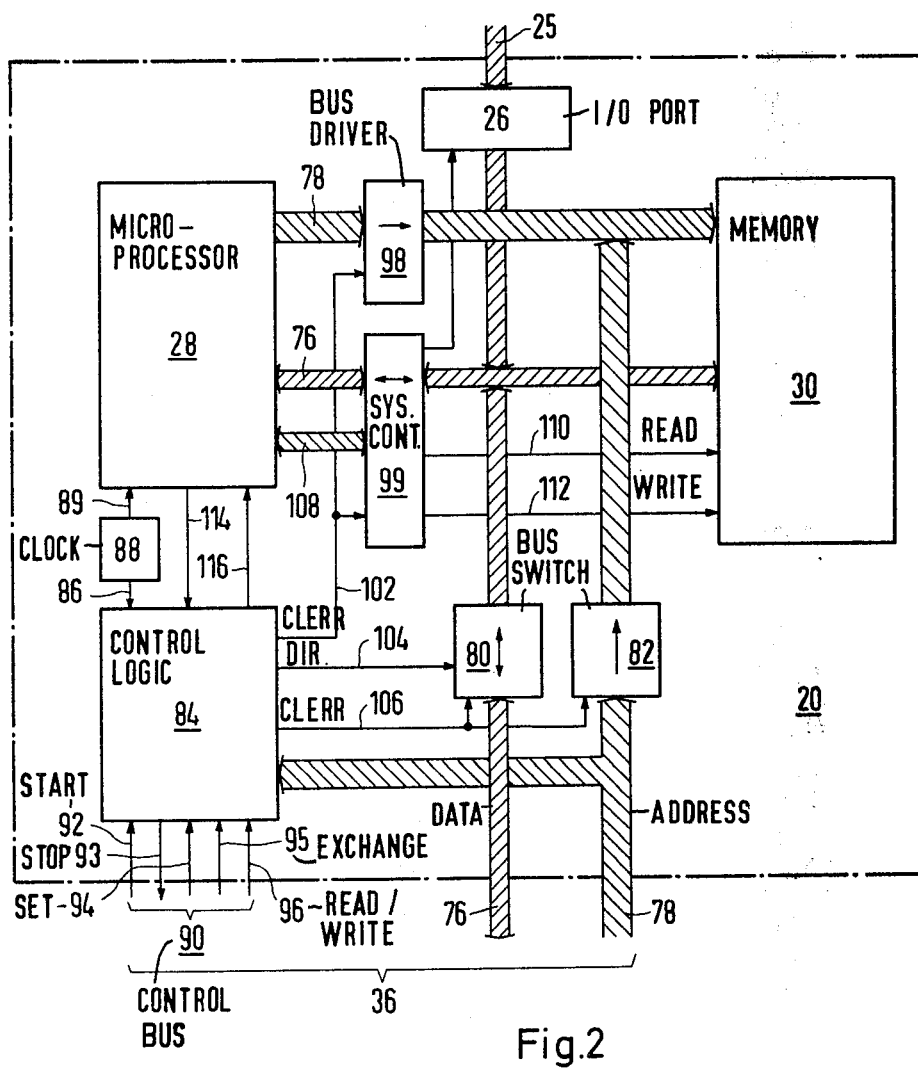
FIG. 2 is a schematic diagram of one of the computer modules.

In the practical embodiment of module 20 according to FIG. 2, the input circuit has the reference symbol 25, the I/O port 26, the microprocessor 28, and the module memory 30, in accordance with FIG. 1. A data bus 76 and an address bus 78 are provided for data traffic. These data circuits contain a bus switch 80 and 82, respectively, coordinated with a common control logic 84. This control logic 84 is connected via a clock circuit 86 to a clock 88 which also provides timing for the microprocessor 28 via a control circuit 89. The control logic 84 receives its switching commands from a control bus 90 which contains a "start" circuit 92, a "stop" circuit 93, a "set switch" circuit 94, and an "exchange" circuit 95 as well as a "read/write" signaling circuit 96. The address bus 78 contains a bus driver 98 and, in addition, a system controller 99 is provided for traffic control from the microprocessor 28 to the module memory 30. The system controller 99 and the bus driver 98 are cleared by a "clearing" circuit 102. The control logic 84 transmits its control signals for data "direction" via a signal circuit 104 and for "clearing" the bus switches 80 and 82 via a circuit 106. The signal input from the microprocessor 28 to the module memory 30 is accomplished by the address bus 78 via the bus driver 98 serving as signal amplifier. The data bus 76 exchanges the signals through the system controller 99 which receives its control signals via a control bus 108. The system controller 99 gives the module memory 30 the "read" signal via a circuit 110 and the "write" signal via a circuit 112. The signal exchange between the microcomputer 28 and the control logic 84 is accomplished via signal circuits 114 and 116.

In the module embodiment according to FIG. 2 the sequence of digital data signals reaches the microprocessor 28 via the input circuit 25 and the I/O port 26 as well as the data bus 76 and the system controller 99. The data are processed and corrected in the microprocessor 28 operating with the program set out below. The corrected data are fed to the module memory 30 via the data bus 76. For folding, the data from the module memory 30 are supplied to the other modules via the data bus 76 and the bus switch 80. The control logic 84 controls the connection of the bus switches 80 and 82 to the data bus 76 and to the address bus 78 respectively, as a function of the control signals it receives via the control bus 90.

In the multiprocessor according to the present invention the modules 20 and 40 are connected to the control computer 60 via the system bus 36. The data are transmitted via the data bus 76 from module to module as well as from the modules to the control computer 60 and vice versa. The coupling memories in the module memories play an important part in this. If a module is supposed to transmit data to all other modules or to the control computer, this data must first be made available in the module's exchange memory. This data are stored in the coupling memories of the addressed modules during the exchange phase.

Only the control computer 60 itself is working during the control phase, recalling the data furnished by the analog-to-digital converters 24 and 44 of the data detectors and possibly buffered. In addition, the control computer 60 determines, during the control phase, the initial state of the computer modules 20 and 40 and advises them of the problem they will have to solve in the next phase. The single computers 28 and 48 of the computer modules 20 and 40 solve the problems given them simultaneously and independently of each other during the subsequent autonomous phase. Then they signal the control computer 60 that they have performed their duty. The information transmission phase commences after the control computer 60 has received a stop signal from all or from a selection of single computers determined by the programs and the circuitry or by the circuitry alone. Generally this is the case when all modules have concluded their autonomous program portion. Controlled by the control computer 60, the data exchange between the coupling memories of the module memories 30 and 50 takes place during the information transmission phase. The data for the image synthesis are generally stored after their computation in the image synthesis memory 70 and can then be supplied to the visual display 72 as needed.

In addition to preprocessing the information, the image synthesis forms part of the data processing. The sequence of digital signals furnished by the detectors 18 of the detector system 8 is first logarithmatized, then cos-weighted and subsequently folded with a predetermined core.

One particularly advantageous embodiment of the image synthesis consists of folding with several permanently stored folding cores. A desirable picture contrast variation is thus obtained. The folding result is again a set of data such as 256 elements.

Each of these preprocessed data then make a contribution to the image synthesis. They are stored in the mass memory 70 serving as image synthesis memory.

At least data folding takes place in a three-phase operation, namely the control phase, the autonomous phase, and the information exchange phase, whereas data detection and data correction of each individual scan may also take place during the antonomous phase only. The coordination of the image addresses for the folded data and possibly also a partial addition already take place expediently during the control phase and the autonomous phase.

One particularly advantageous embodiment of the computer system is obtained when the individual computer modules 20 and 40 are each coordinated with one of the image areas, of which only a few are indicated in FIG. 1 and marked A to H. In the embodiment comprising 256 detectors it is preferable to provide also 256 image areas, each of which is then synthesized by one of the computer modules.

Essentially any mini or microcomputer of 16 bit word size, such as the Siemens 330 or Nova 1200 is suited as control computer 60. The control computer 60 can trigger functions of individual module microprocessors 28 and 48 as well as of groups of microprocessors. The module program is permanently stored in the microprocessor of the respective module in ROM read only memories. The data traffic between the control computer 60 and the module microprocessors 28 and 48 goes indirectly through the module memory 30 or 50, respectively, associated with the single computer. The data from a scan may be processed by the module microprocessors 28 and 48 in three stages, for instance. First the program input data are transferred from the control computer 60 to the memory 30 or 50 of the respective module 20 or 40. Then the input data stored in the module memory 30 or 50 are processed by the associated microprocessor 28 or 48 according to the program permanently stored in the memory, the output data being stored in the module memory or also in a separate coupling memory. Subsequently the program output data are transferred from the module memory 30 or 50 to the control computer 60. The control computer 60 also establishes the connection to the peripheral equipment not shown in FIG. 1, such as data input and data output equipment as well as to the image synthesis memory 70.

The arrangement makes it possible not only to arrive at very short computation times by using fast bipolar components, but costs are also trimmed as compared to fast single processors because conventional, highly integrated standard circuits can be used. Furthermore, due to the design incorporating identical modules, the spare parts inventory and servicing costs are also correspondingly low.

The programs for a typical embodiment to the system, in FORTRAN, are set out below.

```
C
C    |  CONTROL COMPUTER PROGRAM DOTOM
C
     COMMON /MODDAT/ ZEILE(256),IMODUL,IPUNKT,MAXMOD,DALPHA,ALPHA,
    1                HFAECH,FKERN(15),XANF,Y,DX,R,DCHI
     DATA FKERN /-.32,-.16,-.08,-.04,-.02,-.01,-.005,-.0025,
    1 -.00125,-.00064,-.00032,-.00016,-.00008,-.00004,
    2 -.00002,-.00001/
C
C    THE INITIAL VALUES AND PARAMETERS TO BE TRANSFERRED TO THE
C    MODULES ARE STORED IN THIS COMMON BLOCK. 1126 BYTES
C
C    THE VALUES HAVE THE FOLLOWING MEANINGS
C
C       IMODUL     MODULE NUMBER, 1-256, MODULE-DEPENDENT
C       IPUNKT     NUMBER OF IMAGE POINTS PER LINE (SCAN)
C       MAXMOD     NUMBER OF MODULES AVAILABLE
C       ZEILE(256) IMAGE POINTS (256)
C       DALPHA     ANGULAR INCREMENT BETWEEN TWO SCANS IN RADIANS
C       ALPHA      X-RAY SOURCE ANGLE (START=0)
C       HFAECH     SENSOR FAN HALF-ANGLE
C       FKERN(15)  SYMMETRICAL CONVOLUTION COEFFICIENTS
C       XANF       X-VALUE OF FIRST IMAGE POINT
C       Y          Y-VALUE OF FIRST IMAGE POINT, MODULE-DEPENDENT
C       DX         DISTANCE BETWEEN TWO IMAGE POINTS (MM) IN ORIGINAL IMAGE
C       R          DISTANCE BETWEEN X-RAY SOURCE AND TURNING POINT (MM)
C       DCHI       ANGLE BETWEEN TWO SENSORS IN RADIANS
C
C    ADDRESS CONSTANTS FOR COMMUNICATING WITH THE MODULES
C
C       IZEILE     START ADDRESS OF IMAGE LINE REGION, THE PARAMETERS ARE
C                  STORED SEQUENTIALLY AFTER THIS ADDRESS. (789AH = 31642)
```

```
C      IMESSW     START ADDRESS OF MEASUREMENT PROGRAM (4006H = 16390)
C      MESSW      ADDRESS OF MEASURED DATA FIELD (779AH = 30618)
C      IFALT      START ADDRESS OF CONVOLUTION PROGRAM (4106H = 16646)
C      IBILD      START ADDRESS OF IMAGE-RECONSTRUCTION PROGRAM (4206H = 16902)
       IZEILE=31642
       IMESSW=16390
       MESSW =30618
       IFALT =16646
       IBILD =16902
C
C
C      BGROES     IMAGE SIZE (MM) = LENGTH OF ONE SIDE OF ORIGINAL IMAGE
C      NSCAN      NUMBER OF SCANS
C      NSENS      NUMBER OF SENSORS
C
C      SUPPLY MODULES WITH PARAMETERS AND INITIAL VALUES:
C
       BGROES=300.
       NSCAN=360
       NSENS=256
C
       IPUNKT=255
       MAXMOD=255
       DO 1000 I=1,IPUNKT
1000   ZFILE(I)=0.
       DALPHA=3.1415926/180.
       ALPHA=0.
       HFAECH=1.275
       XANF=-BGROESS/2.
       DX=BGROESS/(IPUNKT-1)
       P=700.
       DCHI=2.*HFAECH/(NSENS-1)
       DO 2000 IMODUL=1,MAXMOD
       Y=BGROESS/2. - (IMODUL-1)*DX
       CALL PUTIM(IER,IMODUL,IMODUL,1126,IMODUL)
       IF(IER.NE.0) STOP PUTIM-ERROR
2000   CONTINUE
C
C      FOR ALL SCANS
C
       DO 3000 ISCAN=1,NSCAN
C
C      READ MEASURED VALUES BY STARTING THE MODULE PROGRAMS AT IMESSW
C
       CALL CONTROL(IMESSW,IER)
       IF (IER.NE.0) STOP CONTROL-ERROR MEASURED VALUES
C
C      EXCHANGE MEASURED VALUES
C
       CALL EXCHMM(IER,MESSW,4,1,MAXMOD)
       IF (IER.NE.0) STOP EXCHMM-ERROR MEASURED VALUES
C
C      CONVOLUTION OF THE MEASURED VALUES BY STARTING THE MODULE PROGRAMS
C      AT IFALT
C
       CALL CONTROL(IFALT,IER)
       IF(IER.NE.0) STOP CONTROL-ERROR CONVOLUTION
C
C      EXCHANGE THE CONVOLVED VALUES
C
       CALL EXCHMM(IER,MESSW,4,1,MAXMOD)
       IF(IER.NE.0) STOP EXCHMM-ERROR CONVOLVED VALUES
C
C      IMAGE RECONSTRUCTION
C
       CALL CONTROL(IBILD,IER)
       IF(IER.NE.0) STOP CONTROL-ERROR IMAGE RECONSTRUCTION
C
3000   CONTINUE
C
C      END OF SCAN LOOP
```

```
C
C
C       COLLECTION OF THE PROCESSED IMAGE LINE-BY-LINE FROM THE MODULES
C
        NPJNKT=4*IPUNKT
        DO 4000 IMODUL=1,MAXMOD
        CALL GETFM(IER,IMODUL,IZEILE,IPUNKT,ZEILE)
        IF(IER.NE.0) STOP GETFM-ERROR LINE
C
C       OUTPUT OF THE LINE TO THE SCREEN
C
        CALL DISPLAY(ZEILE,IPUNKT)
C
4000    CONTINUE
        STOP
        END
        COMPILER(1)=5000H
C
C       MODULE PROGRAMS
C
C
C       PROGRAM MESSWERT (COLLECTION OF MEASURED VALUES)
C
        COMPILER(1)=4000H
        COMPILER(3)=7FFFH
C
        REAL DCHI,R,DX,Y,XANF,FKERN(16),HFAECH,ALPHA,DALPHA,ZEILE(256)
        INTEGER*2 MAXMOD,IPJNKT,IMODUL
C
        DIMENSION FELD(256)
C
C
C       READ VALUES THROUGH PORT 06
C
        READ(6) XMESS
C
C       TAKE LOGARITHM
C
        XMESS=ALOG(XMESS)
C
C       INSERT POSSIBLE CORRECTIONS HERE
C
        FELD(IMODUL)=XMESS
        STOP
C
C       THE EXCHANGE OF THE FIELD TAKES PLACE HERE.
C       AFTER THE EXCHANGE, FELD(M) IS THE LOGARITHM OF THE
C       (CORRECTED) MEASURED VALUE OF THE MODULE M
C
C       PROGRAM FALTEN (CONVOLUTION)
C
C
        COMPILER(1)=4100H
1000    DO 2000 I=1,16
        A=0.
        LP=IMODUL+I
        IF(LP.GT.MAXMOD) GOTO 1100
        A=FELD(LP)
1100    B=0.
        LM=IMODUL-I
        IF(LM.LT.1) GOTO 1200
        B=FELD(LM)
1200    CONTINUE
2000    XMESS=XMESS+FKERN(I)*(A+B)
        FELD(IMODUL)=XMESS
        STOP
C
C       EXCHANGE AS ABOVE
C       NOW FELD ONLY CONTAINS CONVOLVED VALUES
C
C
```

```
C       PROGRAM BILDAUFBAU (IMAGE RECONSTRUCTION)
C
C
        COMPILER(1)=4200H
C
        ALPHA=ALPHA+DALPHA
        CA=COS(ALPHA)
        SA=SIN(ALPHA)
        X=XAVF
        DO 3200 I=1,IPUNKT
        XI=CA*X-SA*Y
        ETA=SA*X+CA*Y
        BETA=ATAN(ETA/(XI-R))
        INDEX=(BETA+HFAECH)/DCHI
        DQ=ETA*ETA+(XI-R)*(XI-R)
        ZEILE(I)=ZEILE(I)+FELD(INDEX)/DQ
3200    X=X+DX
        STOP
        END

EXPLANATION OF THE ASSEMBLER SUBROUTINES

PUTIM(IER,MODUL,MODADR,LAENGE,STRADR)
GETFM(IER,MODUL,MODADR,LAENGE,STRADR)
EXCHMM(IER,MODADR,KORBL,MODA,MODE)
CONTROL(STARTADR,IER)
DISPLAY(BILD,ANZAHL)

THE ARGUMENTS HAVE THE FOLLOWING MEANINGS

IER       ERRORCODE 0 = NO ERRORS
MODUL     NUMBER OF MODULE BEING ADDRESSED
MODADR    ADDRESS IN MODULE WHERE DATA IS TO BE READ OR WRITTEN
LAENGE    NUMBER OF BYTES TO BE TRANSFERRED
KORBL     NUMBER OF BYTES TO BE TRANSFERRED PER MODULE
MODA      FIRST TRANSMITTING ('SPEAKER') MODULE
MODE      LAST TRANSMITTING ('SPEAKER') MODULE
STARTADR  MODULE PROGRAM START ADDRESS
BILD      DATA FIELD TO BE OUTPUT TO THE CONSOLE
ANZAHL    NUMBER OF VALUES TO BE OUTPUT TO THE CONSOLE

PUTIM     DATA TRANSFER FROM CONTROL COMPUTER TO MODULE
GETFM     DATA TRANSFER FROM MODULE TO CONTROL COMPUTER
EXCHMM    MULTIPLE EXCHANGE
CONTROL   PROGRAM START
DISPLAY   OUTPUT OF IMAGE TO CONSOLE
```

What is claimed is:

1. A computer system for the image synthesis of a transverse body section with image elements successively transmitted by rays in an image plane in various directions, the rays detected by a plurality of detectors, comprising:
   (a) a plurality of computer modules, one being provided for each of said detectors, each module including a microprocessor, and associated therewith an input-output port for receiving information from a respective detector, a data memory, and a bus switch;
   (b) a common control computer having associated therewith a program memory and an image synthesis memory, said common control computer programmed to control each of said plurality of microprocessors; and
   (c) means interconnecting each of said microprocessors to said common control computer through their respective bus switches.

2. A computer system according to claim 1, wherein all of said microprocessors are connected to a common system bus which is controlled by said common control computer.

3. A computer system according to claim 2, wherein said image synthesis is carried out utilizing both folded data and image information of a part image of the entire transverse body section and wherein each computer module data memory includes capacity for storing both folded data and the image information of a part image of the entire transverse body section.

4. The computer system according to claim 3, wherein said data memory includes a read only memory (ROM) in which the address for each image element is stored and can be recalled.

5. A computer system according to claim 1, wherein said image synthesis is carried out utilizing both folded data and image information of a part image of the entire transverse body section and wherein each computer module data memory includes capacity for storing both folded data and the image information of a part image of the entire transverse body section.

6. The computer system according to claim 5, wherein said data memory includes a read only memory (ROM) in which the address for each image element is stored and can be recalled.

7. The computer system according to claim 1, wherein said data memory includes a read only memory (ROM) in which the address for each image element is stored and can be recalled.

8. A method for the operation of a computer system for the image synthesis of a transverse body section with image elements successively transmitted by rays in an image plane in various directions, the rays detected by a plurality of detectors using apparatus including a plurality of computer modules, one being provided for each of said detectors, each module including a microprocessor, and associated therewith an input-output port for receiving information from a respective detector, a data memory, and a bus switch; a common control computer having associated therewith a program memory and an image synthesis memory, said common control computer programmed to control each of said plurality of microprocessors; and means interconnecting each of said microprocessors to said common control computer through their respective bus switches comprising:
  (a) storing information furnished by the detectors in the memories of their respective computer modules;
  (b) correcting the information stored in said memories simultaneously and independently of each other in each computer module;
  (c) folding the corrected data so obtained in each of the individual computer modules under control of said common control computer; and
  (d) subsequently constructing a partial picture of the entire transverse body section utilizing the folded data from each computer module.

9. The method according to claim 8, wherein at least the folding of the corrected data takes place in a three-phase operation, comprising:
  (a) a control phase during which the control computer only is operating, establishing the initial state of the computer modules and signaling them which problem they will have to solve;
  (b) a succeeding autonomous phase, during which the microprocessors of the computer modules solve the problems assigned to them by their programs simultaneously and independently of each other and then signal the control computer through a stop signal that they have completed their program; and
  (c) an information transmission phase which commences after the control computer has received a stop signal from at least a selection of microprocessors determined by the circuitry and during which, controlled by the control computer, the data exchange between the memories of the computer modules and, if applicable, data storage in the image synthesis memory takes place.

* * * * *